US00PP16636P3

(12) United States Plant Patent
Palmer

(10) Patent No.: US PP16,636 P3
(45) Date of Patent: Jun. 13, 2006

(54) ***ECHINACEA* PLANT NAMED 'CBG CONE3'**

(50) Latin Name: *Echinacea hybrida*
Varietal Denomination: CBG Cone3

(75) Inventor: Angela Jo Palmer, Highland Park, IL (US)

(73) Assignee: Chicagoland Grows, Inc., Glencoe, IL (US)

( * ) Notice: Subject to any disclaimer, the term of this patent is extended or adjusted under 35 U.S.C. 154(b) by 96 days.

(21) Appl. No.: 10/958,234

(22) Filed: Oct. 6, 2004

(65) Prior Publication Data

US 2006/0075530 P1 Apr. 6, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—Buchanan Ingersoll, PC

(57) ABSTRACT

The new cultivar originated as a branch mutation of the 'Art's Pride' cultivar (U.S. Plant Pat. No. 15,090) of unknown causation. Attractive blossoms are formed having yellow-orange ray and disc florets which differ substantially in coloration from those of the 'Art's Pride' cultivar. Also, the blossoms display a blossom fragrance that is more intense than that of the 'Art's Pride' cultivar. Dark green semi-glossy foliage is formed that contrasts nicely with the blossom coloration. The new cultivar is capable of imparting distinctive ornamentation to the landscape.

3 Drawing Sheets

Figures 1, 2, 3, 4, 5, 6, 7, 8:
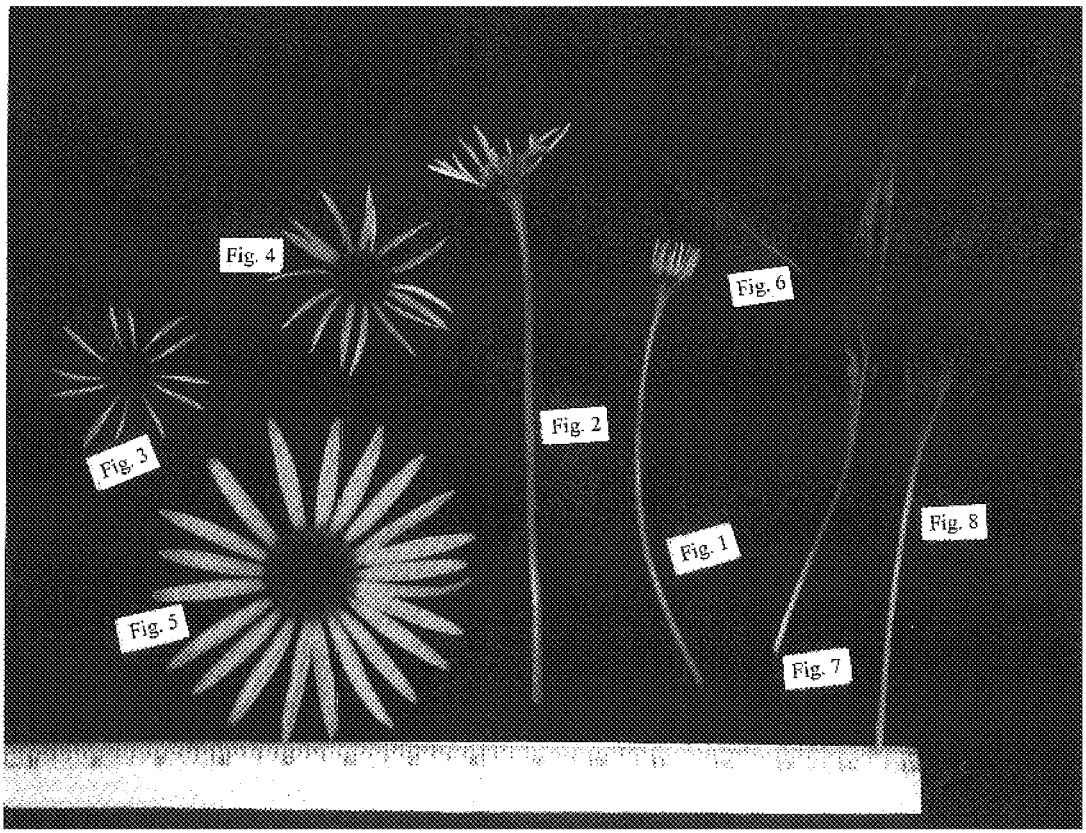

Botanical/commercial classification: *Echinacea hybrida/ Echinacea* Plant.
Varietal denomination: cv. 'CBG Cone3'.

SUMMARY OF THE INVENTION

The invention relates to a new and distinct *Echinacea* plant that was discovered during November 2003 at the Chicago Botanic Garden, Glencoe, Ill., while growing among plants of *Echinacea* 'Art's Pride' cultivar U.S. Plant Pat. No. 15,090, granted Aug. 17, 2004). The new variety is a branch mutation of the 'Art's Pride' variety of unknown causation. The parent 'Art's Pride' variety was the product of controlled breeding program that was carried out by Dr. James R. Ault at the same location.

It was found that the new *Echinacea* cultivar of the present invention possesses the following combination of characteristics:

(a) forms attractive blossoms having yellow-orange ray and disc florets which differ substantially in coloration from those of the 'Art's Pride' cultivar, (b) displays a blossom fragrance of sweet orange-spiced tea that is more intense than that of the 'Art's Pride' cultivar, and (c) forms attractive semi-glossy dark green foliage that contrasts nicely with the blossom coloration.

Also, as previously indicated, the new cultivar of the present invention displays yellow-orange ray and disc florets while the 'Art's Pride' cultivar displays orange ray florets and greyed-purple disc florets. Also, the blossom fragrance of the new cultivar commonly is considerably more intense than that of the 'Art's Pride' cultivar.

The new cultivar can be readily distinguished from *Echinacea purpurea* 'Alba' (non-patented in the United States) and *Echinacea paradoxa* seedling parental plants of the 'Art's Pride' cultivar by the distinctive yellow-orange coloration of the ray florets and the distinctive fragrance of the blossoms. The flowers of *Echinacea purpurea* 'Alba' display greenish disc florets and white ray florets. Also, 'Alba' displays broader foliage. Plants of *Echinacea paradoxa* are known to display yellow ray florets and reddish-brown ray florets, a different blossom fragrance, and a different growth habit.

The new cultivar is well suited for growing as attractive colorful ornamentation in gardens and in the landscape.

Asexual reproduction of the new cultivar by tissue culture was first conducted at Glencoe, Ill., U.S.A. and at Aukland, New Zealand during 2003. This asexual reproduction has demonstrated that the unique combination of characteristics of the new cultivar is firmly fixed and is well retained through successive generations of asexual propagation. Accordingly, the new cultivar asexually reproduces true to type.

The new cultivar also readily undergoes asexual propagation by the rooting of cuttings and by division. Approximately 10 to 12 weeks are required to produce a rooted plant.

The new cultivar has been named 'CBG Cone3'.

BRIEF DESCRIPTION OF THE PHOTOGRAPHS

The accompanying photographs show as true as it is reasonably possible to make the same in color illustrations of this character typical specimens of the plant parts of the new cultivar of the present invention. The depicted plants were approximately two years of age and were growing outdoors under full sun during July at Glencoe, Ill., U.S.A. Dimensions in inches are included at the bottom of FIGS. 1 to 8.

FIG. 1—shows side view of a specimen of a typical bud with emerging ray florets, FIG. 2—shows a side view of a specimen of a typical immature inflorescence, FIG. 3—shows a top view of a specimen of a typical immature inflorescence, FIG. 4—shows a top view of a specimen of a typical inflorescence at intermediate stage of maturity, FIG. 5—shows a top view of a specimen of a more mature inflorescence, FIG. 6—shows a specimen of a sessile leaf obtained at an intermediate location on the stem, FIG. 7—shows a specimen of a typical basal petiolate leaf, FIG. 8—shows a specimen of a typical basal petiolate leaf having another configuration.

Figure 9:
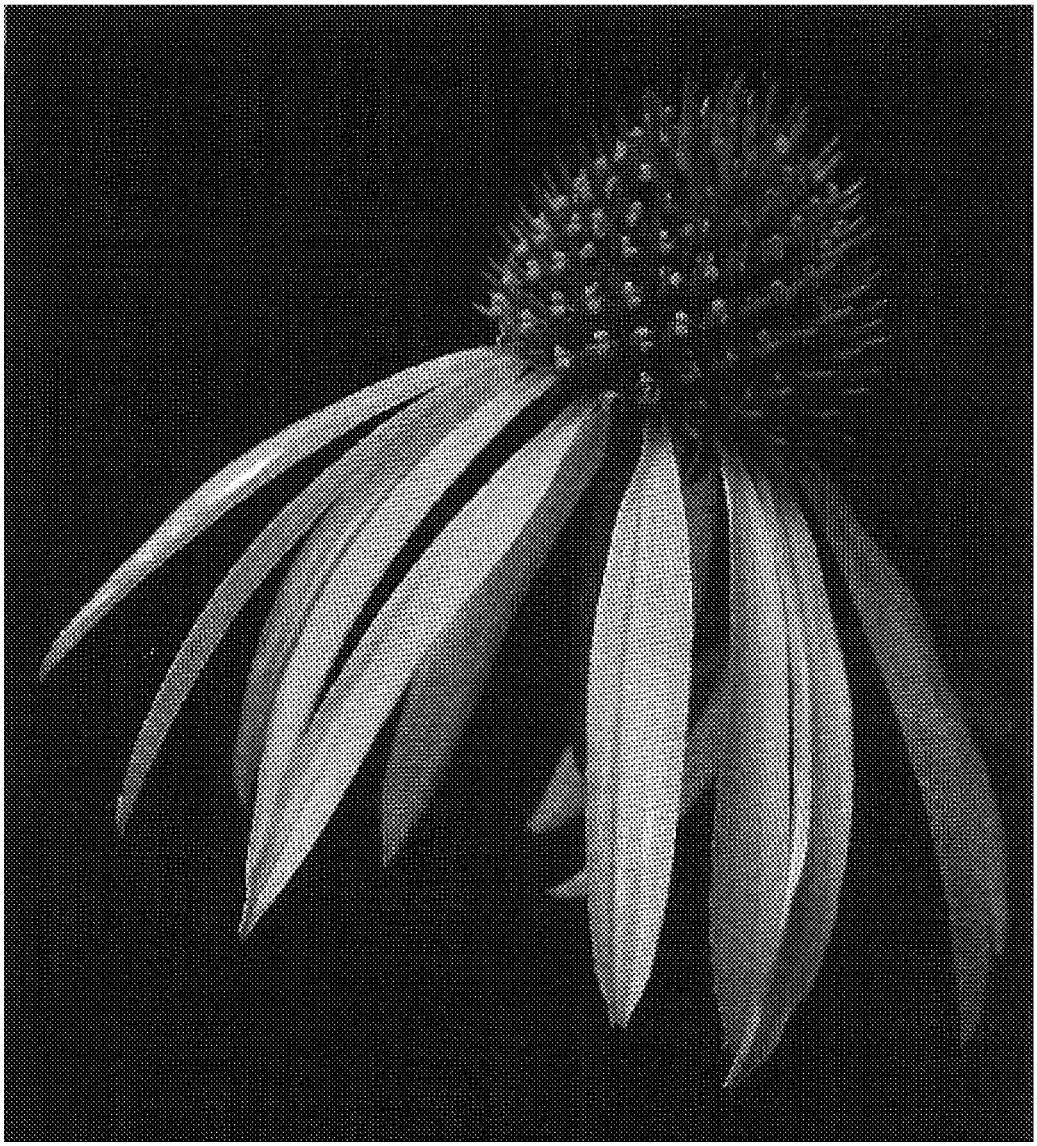
Figure 10:
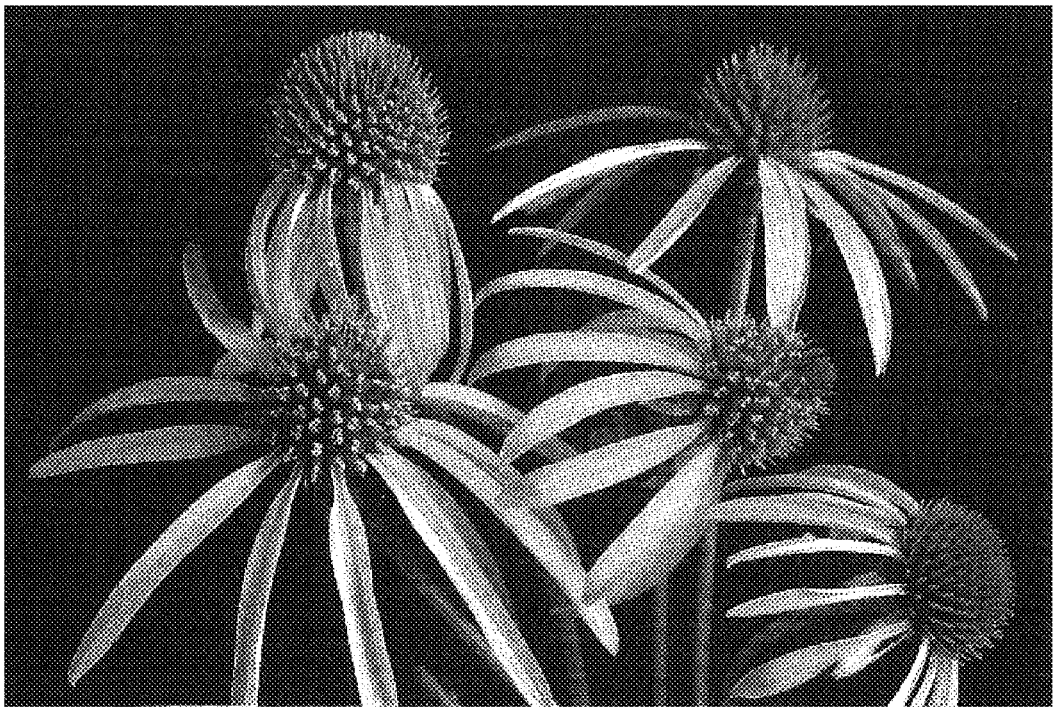

FIG. 9—shows a close side view of a specimen of a fully mature open inflorescence wherein drooping ray florets are shown, and FIG. 10—shows a further close view of a number of blossoms at varying stages of maturity.

DETAILED DESCRIPTION

The following description is based upon the observation of two year-old plants of the new cultivar while growing in an outdoor garden during July under full sun conditions at Glencoe, Ill., U.S.A. The chart used in the identification of the colors is the R.H.S. Colour Chart of The Royal Horticultural Society, London, England.

Plant:

*Height.*—Approximately 70 to 80 cm.

*Width.*—Approximately 60 to 80 cm.

*Lateral branches.*—Length: Approximately 5 to 22 cm. Diameter: Approximately 0.3 to 0.5 cm. Internode length: Approximately 3 to 15 cm. Aspect: Mostly upright. Texture: Roughly strigose pubescent. Color: Yellow-Green Group 145C with striations of Yellow-Green Group 145A.

Foliage:

*Arrangement.*—Alternate, single.

*Mature length.*—Approximately 22 cm on average.

*Mature width.*—Approximately 5 cm at the widest point.

*Shape.*—Narrowly lanceolate, petiolate below, and becoming reduced and sessile at upper locations.

*Apex.*—Acute.

*Base.*—Cuneate.

*Margin.*—Entire to remotely serrated, and undulate (as illustrated in FIGS. 7 and 8).

*Venation pattern.*—Pinnate and predominantly three-veined.

*Texture.*—Somewhat rough and pubescent on both surfaces.

*Color.*—Immature leaf: Upper surface: commonly between Yellow-Green Group 137B and 137C. Under surface: near Green Group 138A. Mature leaf: Upper surface: commonly between Yellow-Green Group 146B and 146C. Under surface: commonly between Yellow-Green Group 146B and 146C. Immature petiole: Yellow-Green Group 145C with striations of Yellow-Green Group 144A. Mature petiole: Yellow-Green Group 145D with striations of Yellow-Green Group 144A, possess a scabrous surface texture, strigose near the stem with oppressed short hairs pointing inwardly and upwardly, primary petioles commonly are approximately 70 cm in length, and secondary petioles branching from primary petioles commonly are approximately 5 to 35 cm in length. Venation: Yellow-Green Group 145B on the upper surface.

Inflorescence:

*Type.*—Capitulum.

*Description.*—Borne upright singly both terminal and axillary on long stout pedicels. The heads are radially symmetrical. Involucre bracts (phyllaries) located below the ray florets are foliaceous, imbricate, lanceolate, and in three series. The ray florets are present in a single series, are sterile, and each possess a single elongated ligule. The disk florets are fertile, are spirally arranged on a conical receptacle, and are individually subtended by chaffy bracts (pales). The pales terminate in a condupliate smooth pointed spine exceeding the length of the disc florets. The heads are persistent.

*Flowering time.*—Continuously and freely commonly from early-July to mid- to late-August.

*Longevity.*—Good color and flower form commonly last approximately 7 to 10 days on the plant, and approximately 5 days when cut and placed in a vase.

*Quantity.*—Free-flowering with approximately 12 to 18 open inflorescences being present on a plant at one time.

*Fragrance.*—Strong, as sweet orange-spiced tea with a hint of honeysuckle fragrance. The fragrance commonly is substantially more intense than that of the 'Art's Pride' cultivar.

*Buds.*—Shape: ovoid when closed. Diameter: approximately 1 to 1.8 cm on average. Color: commonly between Green Group 138A and 138B, and Yellow-Orange Group 21A when first showing color.

*Flower diameter.*—Approximately 1.5 to 2 cm when ray floret coloration first shows, and approximately 12 cm when fully expanded.

*Ray florets.*—Color: on the upper surface Yellow-Orange Group 21A when color begins to appear, a mixture of Yellow-Orange Group 21B, Yellow-Orange Group 23A, and Yellow-Green Group 145A during the course of opening, and in between Yellow-Orange Group 21A and 21B when mature and when fully expanded. The underside of the ray florets when color begins to appear is Yellow-Orange Group 18B, and is Yellow-Orange Group 20B when fully expanded. During development there commonly is a slight hint of yellow-green coloration on the upper surface of the ray florets near where the ray florets attach to the cone. The yellow-green area is small and quickly turns to yellow-orange with maturity. See FIG. 3 in this regard. Length: Approximately 5.5 cm on average. Width: Approximately 1.1 cm on average at the widest point. Shape: Narrowly oblanceolate. Number: Commonly approximately 12 to 18 with a long persistence. Apex: Emarginate and bifid. Base: Acute. Margin: Entire. Texture: Smooth. Orientation: Initially substantially horizontal, and upon maturity commonly droop approximately 30° to 45° or more from the horizontal towards the peduncle.

*Disc florets.*—Color: Mixture of Yellow-Orange Group 21B, Yellow-Orange Group 23A, and Yellow-Green Group 145A during the course of opening; and a mixture of Yellow-Orange Group 23A, Orange Group 24A, and Green Group 138B when fully expanded. Following the emergence of the reproductive organs, the center of the disc commonly assumes a dark brown coloration as shown in FIG. 5. Length: Approximately 0.4 to 0.5 cm on average. Width: Approximately 0.2 cm on average at the widest point. Number: Approximately 170 on average. Diameter: Approximately 0.2 cm on average. Length: Approximately 0.4 cm on average. Shape: Tubular and elongated. Apex: Five-lobed with acute points.

*Phyllaries.*—Length: Approximately 0.7 to 1.4 cm on average. Diameter: Approximately 0.3 to 0.4 cm on average. Shape: Lanceolate and reflexed. Apex: Narrowly acute. Base: Fused. Margin: Entire and strigose pubescent. Texture: Smooth. Number: Approximately 38 on average.

*Pales.*—Length: Approximately 1.5 to 1.7 cm in total, and commonly extend approximately 0.9 to 1.1 cm above the receptacle. Diameter: Approximately 0.1 cm. Shape: Awl-shaped. Apex: Pointed and incurved. Texture: Smooth. Color: Yellow-Green Group 145C at the base, Yellow-Green Group 144B at the middle, and Orange Group 25A at the tip.

*Peduncles.*—Length: Approximately 20 cm on average. Diameter: Approximately 0.3 to 0.5 cm on average. Disposition: Mostly substantially erect. Strength: Relatively strong. Texture: Pubescent. Color: Yellow-Green Group 145A with some Yellow-Green Group 144A.

*Androecium.*—Location: Present only in disc florets. Stamen number: Five per flower. Stamen length: Approximately 0.1 to 0.2 cm on average. Anther color: Yellow-Orange Group 16B. Pollen: Yellow-Orange Group 17A in coloration.

*Gynoecium.*—Location: Present only in disc florets. Pistil number: One. Pistil length: Approximately 0.7 to 0.9 cm on average. Stigma shape: substantially round. Style length: Approximately 0.1 to 0.2 cm. Style color: Yellow-Orange Group 12C. Stigma: Substantially round in cross-section. Stigma color: Yellow-Orange Group 12C.

*Fruit.*—Type: Cypselae (achene). Quantity: One per inflorescence. Length: Approximately 0.4 to 0.6 cm. Shape: Substantially quandrangular. Size: Approximately 0.3 cm across at distal end. Color: Brown Group 200A with some stripes of Grey-Brown Group 199A.

*Seeds.*—Quantity: One per fruit. Length: Approximately 0.3 to 0.4 cm. Diameter: Approximately 0.2 cm. Color: Orange-White Group 159A with a base of Greyed-Orange Group 164A.

No particular resistance to pathogens and pests commonly encountered with *Echinacea* plants has been noted to date when observing plants of the new cultivar being grown at Glencoe, Ill., U.S.A.

The new cultivar of the present invention has withstood temperatures as low as −15° F. and has tolerated temperatures as high as 100° F.

The new 'CBG Cone3' cultivar has not been observed to date under all possible environmental conditions. Accordingly, it is possible that the phenotype may vary somewhat with variations in the environment, such as temperature, light intensity, day length, and other cultural conditions without variance of the genotype.

I claim:

1. A new and distinct *Echinacea* plant having the following combination of characteristics:

(a) forms attractive blossoms having yellow-orange ray and disc florets which differ substantially in coloration from those of the 'Art's Pride' cultivar (U.S. Plant Pat. No. 15,090), (b) displays a blossom fragrance of sweet orange-spiced tea that is more intense than that of the 'Art's Pride' cultivar, and (c) forms attractive semi-glossy dark green foliage that contrasts nicely with the blossom coloration;

substantially as herein shown and described.

* * * * *